US012697216B2

(12) United States Patent (10) Patent No.: US 12,697,216 B2
Genovese et al. (45) Date of Patent: Aug. 4, 2026

(54) SYSTEMS, DEVICES AND METHODS INCLUDING RETRIEVABLE TISSUE ANCHOR

(71) Applicant: Medtronic, Inc., Minneapolis, MN (US)

(72) Inventors: Matthew E. Genovese, Windsor, CA (US); Caitlin M. Owenson, Santa Rosa, CA (US); Emily A. Grimm, Petaluma, CA (US); William A. Berthiaume, Santa Rosa, CA (US); Karan P. Punga, San Rafael, CA (US); William W. Chang, Santa Rosa, CA (US); Fatemeh Fatemi Far, Richmond, CA (US)

(73) Assignee: Medtronic, Inc., Minneapolis, MN (US)

( * ) Notice: Subject to any disclaimer, the term of this patent is extended or adjusted under 35 U.S.C. 154(b) by 416 days.

(21) Appl. No.: 18/571,235

(22) PCT Filed: Jun. 20, 2022

(86) PCT No.: PCT/IB2022/055724
§ 371 (c)(1),
(2) Date: Dec. 17, 2023

(87) PCT Pub. No.: WO2022/269472
PCT Pub. Date: Dec. 29, 2022

(65) Prior Publication Data
US 2024/0285406 A1 Aug. 29, 2024

Related U.S. Application Data

(60) Provisional application No. 63/212,942, filed on Jun. 21, 2021.

(51) Int. Cl.
*A61F 2/24* (2006.01)
(52) U.S. Cl.
CPC .......... *A61F 2/2445* (2013.01); *A61F 2/2466* (2013.01); *A61F 2220/0016* (2013.01); *A61F 2220/0091* (2013.01)
(58) Field of Classification Search
CPC .................. A61F 2/2445; A61F 2/2466; A61F 2220/0016; A61F 2220/0091;
(Continued)

(56) References Cited

U.S. PATENT DOCUMENTS 5,423,857 A 6/1995 Rosenman et al.
5,728,116 A 3/1998 Rosenman
(Continued)

FOREIGN PATENT DOCUMENTS

WO 2005046488 A2 5/2005
WO 2010030842 A2 3/2010

OTHER PUBLICATIONS

International Search Report and Written Opinion, International Application No. PCR/IB2022/055724, mailed Oct. 5, 2022.

*Primary Examiner* — Richard G Louis
(74) *Attorney, Agent, or Firm* — Medler Ferro Woodhouse & Mills PLLC

(57) ABSTRACT

Aspects of the disclosure include systems including an anchor including a body having a distal end, a proximal end and an opening extending from the proximal end to the distal end. The distal end includes a plurality of flanges, each flange including a proximal barb and a distal barb; the anchor having a natural arrangement in which the distal barbs of the plurality of flanges converge to form a pointed tip. The system further includes a rod that can be inserted in the opening to force the distal barbs away from a longitudinal axis of the opening into a delivery arrangement. The (Continued)

rod can also be used to retrieve an anchor after deployment. Such anchors can be utilized with annuloplasty implants. Methods of deploying and retrieving anchors of the disclosure are also disclosed.

20 Claims, 10 Drawing Sheets

(58) Field of Classification Search
CPC ......... A61F 2/2448; A61B 2017/00243; A61B 2017/00867; A61B 2017/0409; A61B 2017/0411; A61B 2017/0414; A61B 2017/0435; A61B 2017/0437; A61B 2017/0496; A61B 17/0401
See application file for complete search history.

(56) References Cited

U.S. PATENT DOCUMENTS

| | | | |
|---|---|---|---|
| 8,968,393 B2 | 3/2015 | Rothstein | |
| 9,192,472 B2 | 11/2015 | Gross et al. | |
| 9,241,710 B2 | 1/2016 | Paz et al. | |
| 9,622,862 B2 | 4/2017 | Lashinski et al. | |
| 10,368,870 B2 | 8/2019 | Ranucci et al. | |
| 2004/0093024 A1 | 5/2004 | Lousararian et al. | |
| 2015/0305738 A1 | 10/2015 | Thomas | |
| 2019/0343626 A1 | 11/2019 | Smirnov et al. | |
| 2019/0350710 A1 | 11/2019 | Ketai et al. | |
| 2021/0113212 A1 | 4/2021 | Lashinski et al. | |

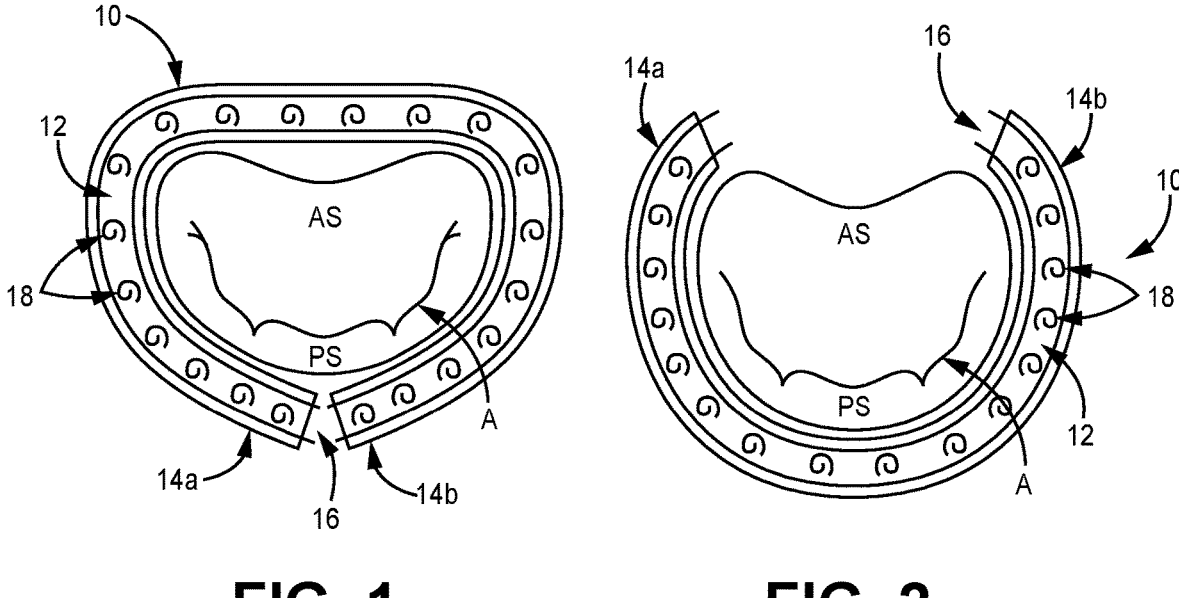
FIG. 1        FIG. 2
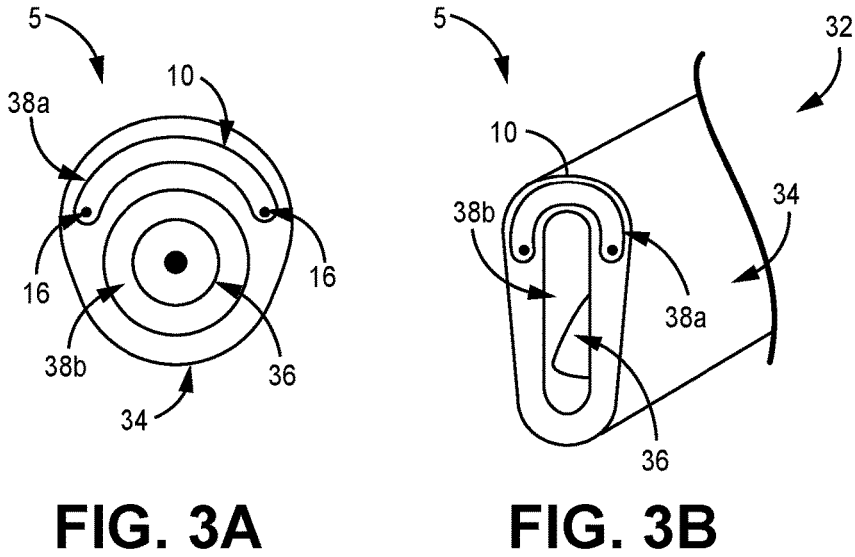
FIG. 3A        FIG. 3B

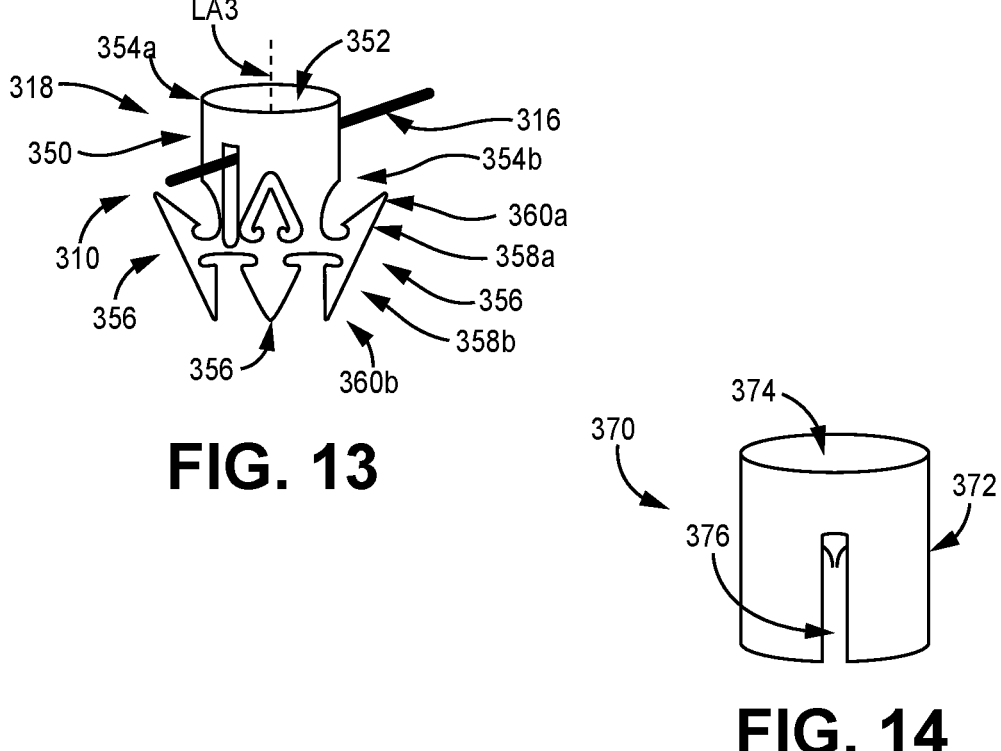
FIG. 13
FIG. 14
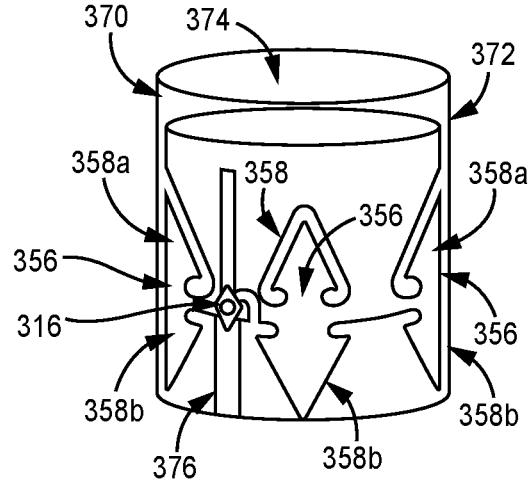
FIG. 15

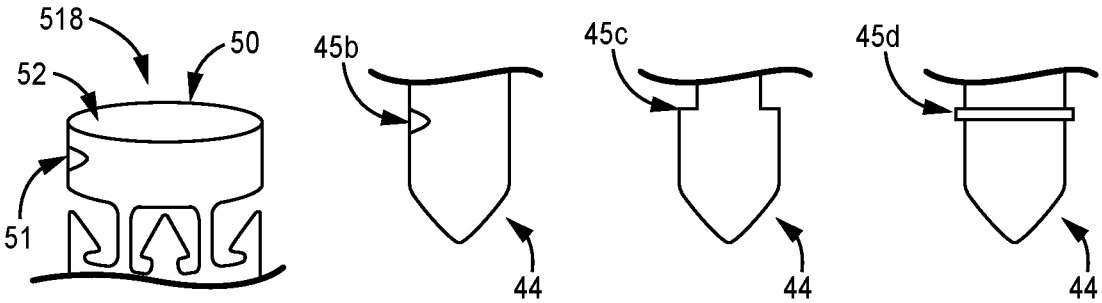
FIG. 19     FIG. 20     FIG. 21     FIG. 22
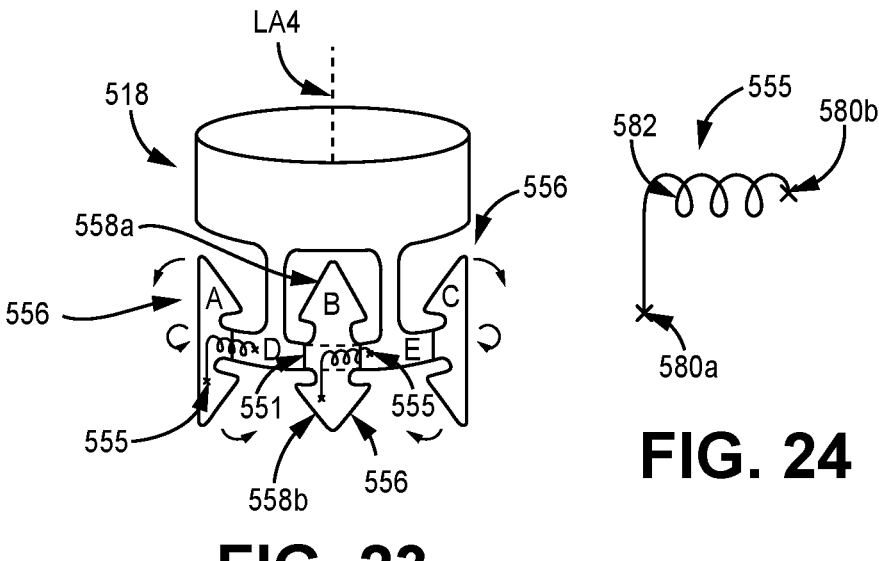
FIG. 23
FIG. 24

SYSTEMS, DEVICES AND METHODS INCLUDING RETRIEVABLE TISSUE ANCHOR

FIELD

The present technology is generally related to annulus repair methods, systems and devices including heart valve annulus repair devices having tissue anchors.

BACKGROUND

Generally, the anatomy and physiology of the human heart is well known. Of the four one-way valves in the heart, the two inlet valves are the mitral valve of the left side of the heart, and the tricuspid valve on the right side of the heart. The tricuspid valve is located between the right atrium and the right ventricle. The three leaflets of the tricuspid valve laterally terminate at the tricuspid annulus. Blood flows from the superior and inferior vena cava into the right atrium, then through the tricuspid valve during diastole to fill the right ventricle. During ventricular systole, the tricuspid valve is closed and blood is ejected through the pulmonary valve into the pulmonary artery and hence through the lungs. At the end of ventricular systole the pulmonary valve closes. Leaving the lungs, the now oxygenated blood flows into the left atrium and hence through the mitral valve into the left ventricle during ventricular diastole. Finally, at ventricular systole the mitral valve closes and blood is ejected through the aortic valve into the aorta. However, should the mitral valve become regurgitant due to disease then some percentage of the left ventricular stroke volume will flow backwards through the mitral valve into the left atrium. This regurgitation causes the left atrial pressure to rise, in turn causing pulmonary artery pressure to rise, which is reflected back to the right ventricular pressure.

Typically, to treat a patient with functional mitral regurgitation, a physician places an annuloplasty ring on the mitral annulus to reduce the circumference and septal-lateral diameter of the annulus. In degenerative mitral regurgitation patients, annuloplasty rings are utilized to stabilize the mitral annulus, not reduce the annular circumference.

The present disclosure addresses problems and limitations associated with the related art.

SUMMARY

The techniques of this disclosure generally relate to systems, devices and methods of delivering one or more anchors into tissue and, optionally, retrieving one or more deployed anchors from the tissue. In some aspects of the disclosure, the anchors are part of an annuloplasty implant, which is delivered to a valve annulus to treat mitral valve regurgitation. Various examples of the disclosure include anchors that can be retrieved from tissue, if desired.

In one aspect, the present disclosure provides a system including an anchor including a body having a distal end, a proximal end and an opening extending from the proximal end to the distal end. The distal end includes a plurality of flanges, each flange including a proximal barb and a distal barb: the anchor having a natural arrangement in which the distal barbs of the plurality of flanges converge to form a pointed tip. The system further includes a rod that can be inserted in the opening to force the distal barbs away from a longitudinal axis of the opening into a delivery arrangement.

In another aspect, the disclosure provides a method including providing a delivery device including an anchor and an anchor delivery apparatus including a rod having a distal tip. The anchor includes a body having a distal end, a proximal end and an opening extending from the proximal end to the distal end. The distal end includes a plurality of flanges, each flange including a proximal barb and a distal barb. In various methods, the rod is inserted through the opening such that the distal barbs and proximal barbs are positioned along an outer surface of the rod in a delivery arrangement. The method further includes positioning the distal tip of the rod at a first location at tissue within a human body and distally advancing the anchor off of the rod and at least partially into the tissue such that the anchor transitions to a natural arrangement in which the proximal barbs engage the tissue and the distal barbs converge toward a longitudinal axis of the opening. Methods can further include distally advancing the rod into the opening to force the distal barbs away from the longitudinal axis of the opening and the proximal barbs toward the longitudinal axis of the opening so that the anchor can be repositioned or removed.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1 is a schematic illustration of an implant positioned around a mitral valve annulus in a first orientation.

FIG. 2 is a schematic illustration of the implant of FIG. 1 positioned around the mitral valve annulus in a second orientation.

FIG. 3A is an end view of a delivery device having an anchor delivery apparatus that can be used to deliver the implant of FIGS. 1-2.

FIG. 3B is a partial, perspective view of the delivery device of FIG. 3A having a first lumen and a second lumen.

FIG. 13 is a partial, perspective view of an implant that can be used with the delivery device of FIG. 12.

FIG. 14 is a side view of an alternate anchor housing that can be used with the delivery device of FIG. 12 and the implant of FIG. 13.

FIG. 15 is a side view of the anchor housing of FIG. 14 (shown as transparent) that is housing the anchor of FIG. 13.

FIG. 19 is a partial, schematic illustration of an alternate anchor.

FIGS. 20-22 are partial, schematic illustrations of rods having alternate protrusions configured to engage the anchor of FIG. 19.

FIG. 23 is an alternate anchor of the disclosure.

FIG. 24 is a schematic view of a spring of the anchor of FIG. 23.

DETAILED DESCRIPTION

Figure 4:
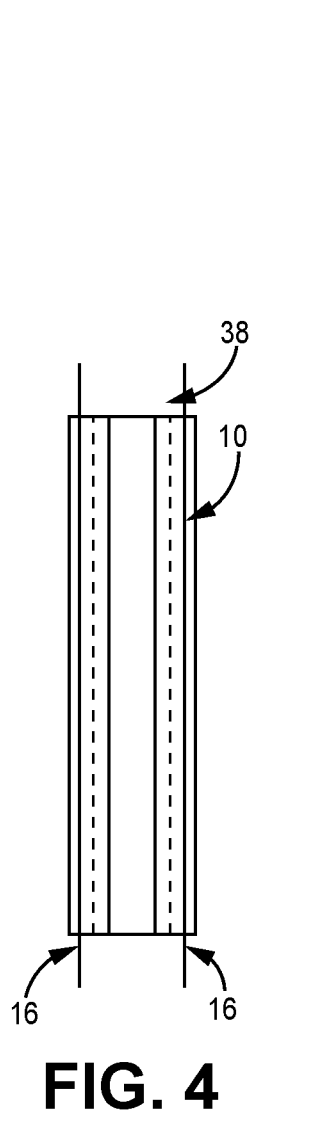
FIG. 4 is a partial, schematic view of the implant within the first lumen of the delivery device of FIGS. 3A-3B.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

FIG. 1 schematically illustrates one non-limiting implant 10 of the disclosure positioned around a mitral valve annulus A. The implant 10 includes a length of material 12 having first and second ends 14a, 14b. The material 12 can be woven or fabric, for example. In this embodiment, both ends of the implant 10 are positioned at the posterior side PS of the annulus A. The implant 10 includes at least one cinching member 16 that extends through the material 12, from one end to the other 14a, 14b. Once the implant 10 is secured to the annulus A with a plurality of anchors 18 (generally referenced), the cinching member 16 can be proximally tensioned and locked in position to resize the annulus A for treatment of valve regurgitation, for example. Similarly, as shown in FIG. 2, the ends 14a, 14b of the material 12 of the implant 10 can be positioned at the anterior side AS of the annulus A, as desired. It will be understood that other bodily lumens can be resized in a similar manner with similar implants and the present disclosure is not intended to be limited to any particular human bodily lumen.

Referring now in addition to FIGS. 3A-3B, which illustrate a system 5 including a delivery device 32 for housing the implant 10 and an anchor delivery apparatus 36. In this example, the delivery device 32 includes a catheter 34 defining a first lumen 38a to receive the implant 10 (see also, FIGS. 1-2 and 4) and a second lumen 38b to receive the anchor delivery apparatus 36 (see also, FIG. 5). The anchor delivery apparatus 36 can be of any of the types disclosed herein. In one example, the anchor delivery apparatus 36 includes a catheter 40 having a threaded interior surface 42 (schematically represented). The anchor delivery apparatus 36 can house a plurality of stacked or nested anchors 18 (only a few of which are referenced) and a rod 44 that extends through each of the anchors 18. Each anchor 18 can include a head or body 50 that includes corresponding threads (not visible) so that rotational advancement of the anchor 18 moves the anchor along the threaded interior surface 42 of the catheter 40. The anchor delivery apparatus 36 can further include a backstop 46 positioned within the catheter 40 that restricts or blocks proximal movement of the stacked anchors 18. Additional details regarding how the delivery device 32 can optionally be configured can be found in U.S. Provisional Application Ser. No. 63/184,470, the disclosure of which is hereby incorporated by reference.

Figure 5:
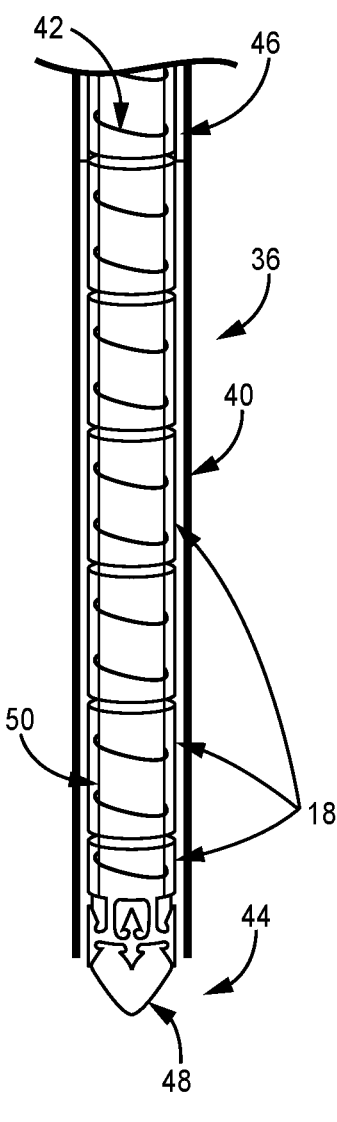
FIG. 5 is a partial, schematic illustration of an anchor delivery apparatus that can be positioned within the second lumen of the delivery device FIGS. 3A-3B.
Figure 6:
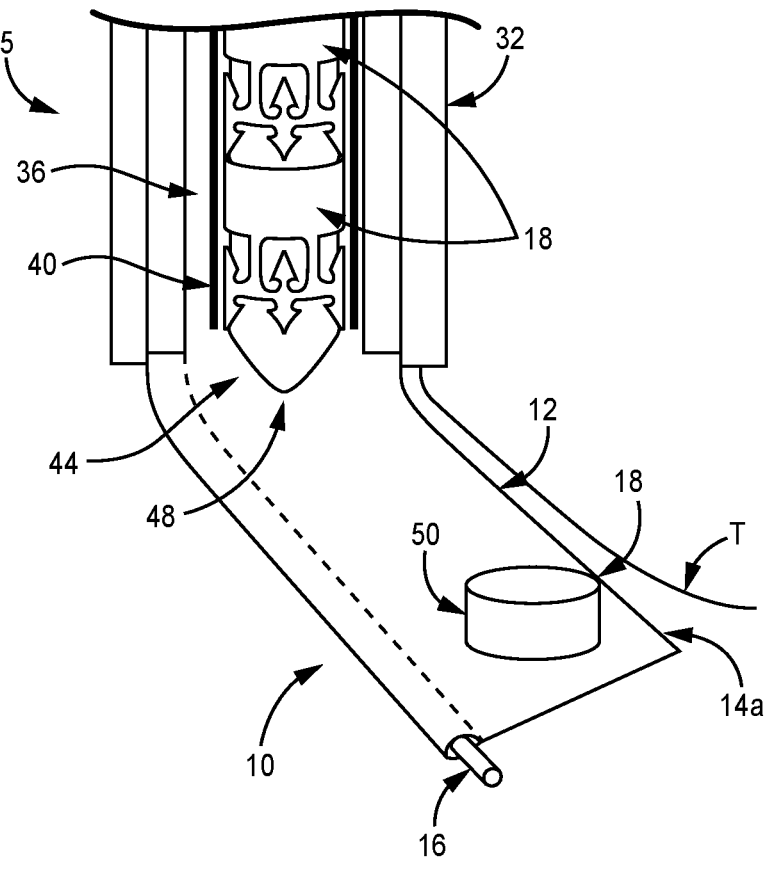
FIG. 6 is a partial, schematic illustration of the delivery device of FIGS. 3A-3B deploying a plurality of anchors of the anchor delivery apparatus of FIG. 5 into the implant.

The rod 44 of the anchor delivery apparatus 36 can serve to both advance the plurality of anchors 18 and also can be utilized to retrieve a deployed anchor 18 from tissue, as desired. In the example of FIG. 5, the rod 44 includes a pointed or tapered distal tip 48. Referring in addition to FIG. 6, as the implant 10 is dispensed from the first aperture 38a, the anchor delivery apparatus 36 can be used to deploy one anchor 18 through the material 12 of the implant 10 to secure the implant 10 to tissue T (which can be annulus A in some examples). As the distalmost anchor 18 is deployed into the tissue T at a first location, the next anchor 18 can be distally advanced from within the catheter 40 with the rod 44 and deployed though the material 12 at a second location of the tissue T until the implant 10 is sufficiently secured to the annulus, tissue or other bodily lumen (e.g., see FIGS. 1-2). The placement of each anchor 18 can be selected to optionally cinch or resize the annulus around which the implant 10 is being positioned.

Various anchors 18 of the disclosure are configured to be retrievable after being deployed at least partially into tissue. One such example is shown in detail in FIGS. 7A-7B. The anchor 18 has the head or body 50 that defines an opening 52 between a proximal and distal end 54a, 54b of the body 50 for the rod 44 to be positioned. In this example, the anchor 18 includes a plurality of flanges 56 spaced about the body 50, each flange 56 can include opposing proximal and distal barbs 58a, 58b. Only one flange 56 is referenced in FIGS. 7A-7B for ease of illustration, however, each flange 56 can be identically configured. The number of flanges 56 can vary. In the illustrated example, the anchor 18 includes three flanges 56 equally spaced around the circumference of the body 50. Each barb 58a, 58b may terminate at a pointed tip 60a, 60b. Collectively, the tips 60b of the distal barbs 58b converge toward a longitudinal axis LA1 of the opening 52 to form a pointed tip of the anchor 18 when the anchor is in the deployed configuration of FIG. 7B. In one example, the flanges 56 are cut from a material forming the anchor 18 so that the anchor 18 is integrally formed of a unitary piece of material. Each anchor 18 has a pre-deployment or delivery arrangement (FIG. 7A) in which the flanges 56 are urged against or in-line with the proximal end 54a of the body 50 by the catheter 40 and/or the rod 44. Each anchor 18 further includes a deployed or natural arrangement (FIG. 7B) in which the proximal barbs 58a are freed from the restriction of the catheter 40 and the distal barbs 58b are released from the rod 44 so that the distal barbs 58b pivot toward the longitudinal axis LA1 and the proximal barbs 58a and extend outwardly and away from the longitudinal axis LA1.

In some examples, the proximal and distal barbs 58*a*, 58*b* are configured such that the rod 44 pushing the distal barbs 58*b* outwardly correspondingly pivots the proximal barbs 58*a* inwardly to an opposite degree. In one example, the flanges 56 are made of a shape memory material or metal, such as nitinol, so that the flanges 56 are biased in the deployed arrangement of FIG. 7B. The flanges 56 are configured to collectively engage and retain the anchor 18 within the tissue or annulus after deployment.

Figures 7A, 7B:
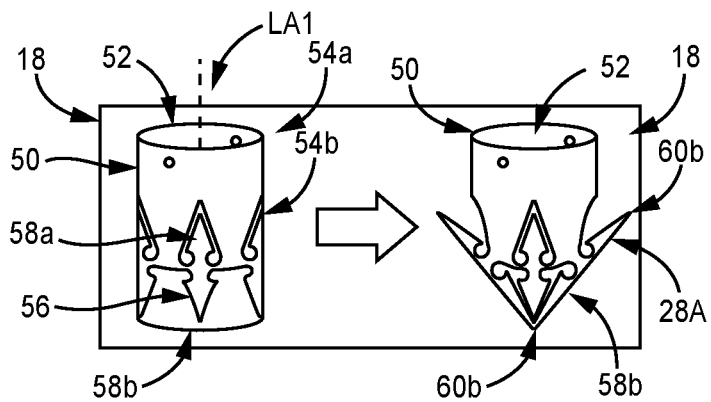
FIG. 7A is a side view of the anchor of FIG. 6 that can be used with the systems, devices and methods of the disclosure in a delivery arrangement.
FIG. 7B is a side view of the anchor of FIG. 7B in a natural or deployed arrangement.

Should removal or repositioning of the anchor 18 be desired, various anchors 18 and systems 5 of the disclosure are configured such that the flanges 56 can be brought back into the pre-deployment or delivery arrangement of FIG. 7A after the anchor 18 has been deployed at least partially into tissue. In one example, to retrieve a deployed anchor 18, the rod 44 is distally advanced through the opening 52 in the body 50 such that the rod 44 pushes the distal barbs 58*b* to the pre-deployment arrangement, which correspondingly pivots the proximal barbs 58*a* back into alignment with the proximal end 52*a* of the body 50. Once the anchor 18 is in the pre-deployment arrangement, it can be proximally withdrawn from tissue, causing less damaged to the tissue as compared to a method in which an anchor is attempted to be proximally withdrawn with flared barbs or the like engaged with tissue.

Figure 8:
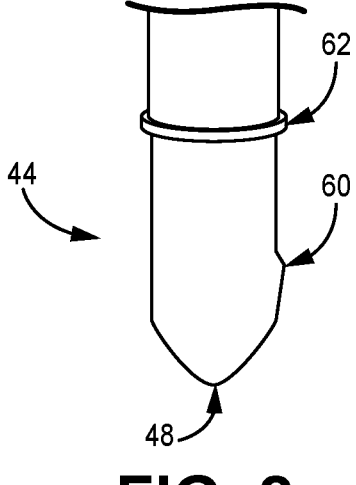
FIG. 8 is a partial, side view of a rod that can be used to deliver and retrieve the anchor of FIGS. 7A-7B.
Figure 9:
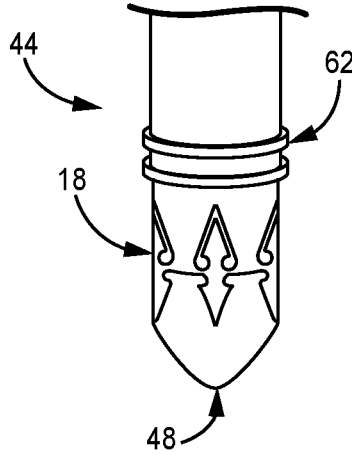
FIG. 9 is a partial, side view of the rod of FIG. 8 engaged with the anchor of FIGS. 7A-7B.

Referring now in FIGS. 8-9, in some examples of the disclosure, the rod 44 includes a depressible tab 60 that can engage the anchor 18 during delivery and retrieval. In one example, the tab 60 is made of a resilient material or is otherwise biased outwardly to a position that is not depressed as shown in FIG. 8. During delivery, the tab 60 is positioned distal to the anchor 18 to maintain the anchor on the rod 44. At this stage, the tab 60 is not depressed. As the distal tip 48 is advanced into tissue T, the tab 60 will be depressed by the tissue so that the anchor 18 can be distally advanced off of the rod 44. During retrieval, the tab 60 is depressed within the opening of the anchor 18 until the tab 60 distally passes the anchor. Then, the tab 60 can pop back out and engage the anchor 18 so that proximal movement of the rod 44 will translate to the anchor 18 as the tab 60 pushes the anchor 18. In instances where merely passing the tab 60 distally past the anchor 18 or 118 does not result in the tab popping back out radially—such as, for example, due to force of surrounding tissue preventing radial pop-out—a mechanism similar to what is shown in FIG. 10F may be used. With this mechanism, the rod 44 would be hollow, and permit a further internal rod 57, with an outer diameter close to or equal to the internal diameter of the hollow rod 44, to pass within the hollow rod 44 to a point at or near the distal tip. This further internal rod 57 would force the tab 60 to pop radially outward and engage the anchor 18 (depicted as 118 in FIG. 10F) so that proximal movement of the rod 44 will translate to the anchor 18 (or 118) as the tab 60 pushes the anchor 18 (or 118). In other examples, the rod 44 can optionally further include an annular lip 62 or the like to assist in pushing the anchor 18 though tissue and prevent proximal movement of the anchor 18 along the rod 44 during deployment off of the rod 44. The lip 62 is particularly suitable for delivery methods in which anchors 18 are not stacked or nested on the rod 44 for delivery but are delivered one at a time or in systems where one rod 44 is provided for each anchor 18.

Figure 10A:
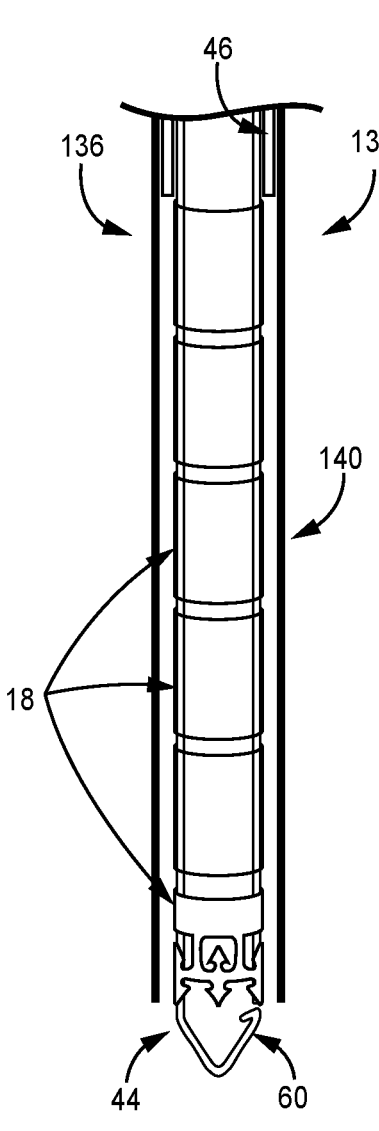
FIG. 10A is a partial, schematic illustration of an anchor delivery apparatus having a plurality of stacked anchors.
Figure 10B:
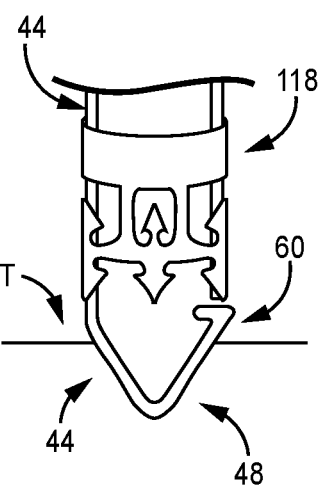
FIGS. 10B-10D are a partial, schematic illustrations of the anchor delivery apparatus of FIG. 10A advancing a distal-most anchor into tissue.
Figure 10C:
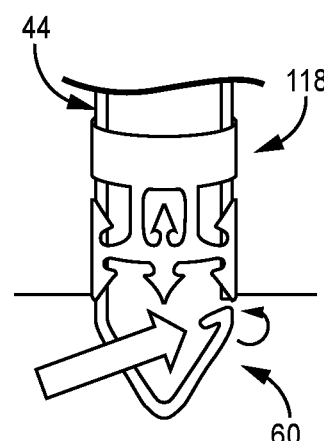
Figure 10D:
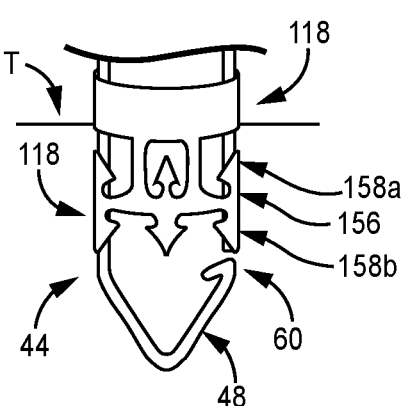
Figure 10E:
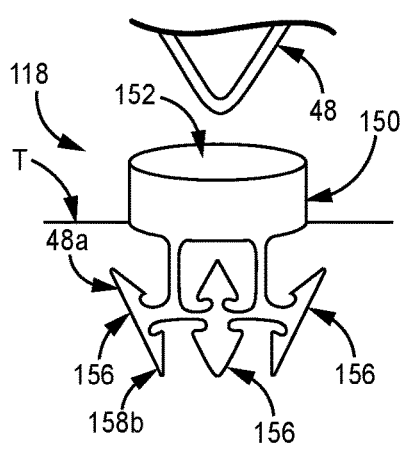
FIGS. 10E-10F are schematic illustrations of a retrieval method of the distalmost anchor of FIG. 10D.
Figure 10F:
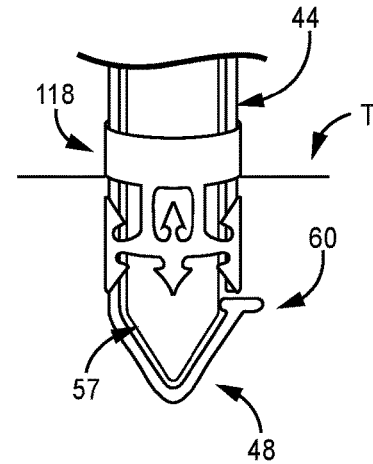

Referring now in addition to FIGS. 10A-10E which illustrate use of a delivery device 132 including an anchor delivery apparatus 136 having the rod 44 having with tab 60. In this example, the delivery device 132 includes a catheter 140 that does not include the optional threaded interior surface provided in the embodiment of FIG. 5. The catheter 140 can otherwise be similarly configured to catheter 40. As shown in FIG. 10A, the anchor delivery apparatus 136 can be provided within the catheter 140 in a delivery arrangement in which a plurality of anchors 118 (generally referenced) are positioned on the rod 44. In some examples, the plurality of anchors 118 will be nested on the rod 44. The tab 60 is posted distal to the plurality of anchors 118 and engages the distalmost anchor 118 to maintain the plurality of anchors on the rod 44. A backstop 146 can be provided within the catheter 140 to restrict proximal movement of the plurality of anchors 118, particularly as the anchors are driven into tissue. In FIG. 10B, the distal tip 48 of the rod 44 is directed to a first target site and then is inserted into tissue T. In FIG. 10C, as the tab 60 is advanced into the tissue T, the tab 60 is depressed so that the distalmost anchor 118 can be distally advanced over the tab 60 and into the tissue T (FIG. 10D). When the anchor 118 is sufficiently advanced at least partially into the tissue T, the rod 44 can be withdrawn through the opening 152 leaving the anchor 118 within tissue T. Once freed from the rod 44, the anchor 118 automatically transitions to its natural, deployed state (FIG. 10E) in which distal barbs 158*b* converge toward each other and proximal barbs 158*a* flare outwardly from a longitudinal axis LA2 to engage and maintain the anchor 18 within the tissue T. In some examples, one or more anchors 118 will be deployed through an implant (e.g., implant 10) and then into tissue T, to secure the implant 10 to the tissue T. As shown in FIG. 10F, to optionally retrieve the anchor 118, the rod 44 can be reinserted into the opening 152, which will depress the tab 60 until the tab 60 distally exits the anchor 118. At that point, the tab 60 will extend to its expanded arrangement and can be used to engage and pull the anchor 118 proximally to dislodge the anchor 118 from the tissue. As mentioned previously, in instances where merely passing the tab 60 distally past the anchor 18 or 118 does not result in the tab popping back out radially—such as, for example, due to force of surrounding tissue preventing radial pop-out—a mechanism similar to what is shown in FIG. 10F may be used, with the further internal rod 57 inserted within the rod 44 to force the tab 60 radially outward to engage anchor 118 or 18. Alternatively, the further internal rod 57 may not be required in certain scenarios. For example: if tab 60 were designed such that initial entry into tissue provided enough force to depress it inward, but subsequent exposure to tissue may result in the tab 60 popping back out, then after initial entry of tip into tissue and depression of the tab 60 (as shown in FIG. 10C), the distal end of anchor 118 or 18 could be slid slightly distally relative to the tab 60 as part of the deployment process. Thus, anchor 118 or 18 would be partially radially surrounding tab 60, keeping it depressed. If recapture were desired, then the rod 44 could be slightly advanced relative to anchor 118 or 18, so that the tab 60 is once again distally past anchor 18 or 118 and able to pop back out. To further assist in dislodging the anchor 118 from the tissue T, insertion of the rod 44 within the opening 152 will push distal barbs 158*b* apart to corresponding pull in the proximal barbs 158*a* to the arrangement of FIG. 10F.

Figure 11A:
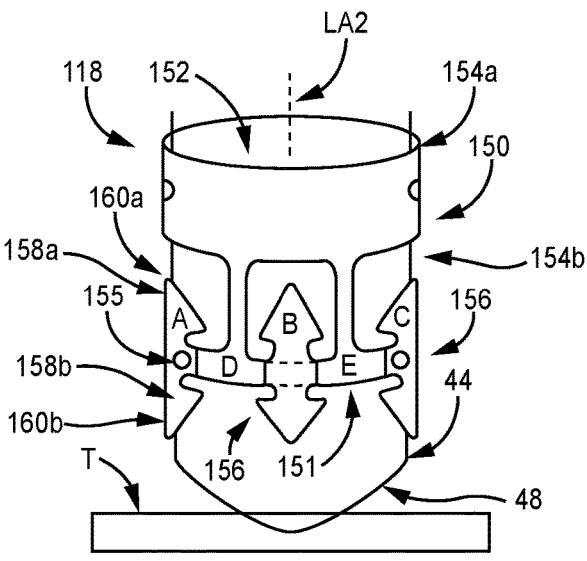
FIG. 11A is a partial, enlarged side view of the anchor and rod of FIGS. 10A-10F that can be part of systems of the disclosure in a delivery arrangement.
Figure 11B:
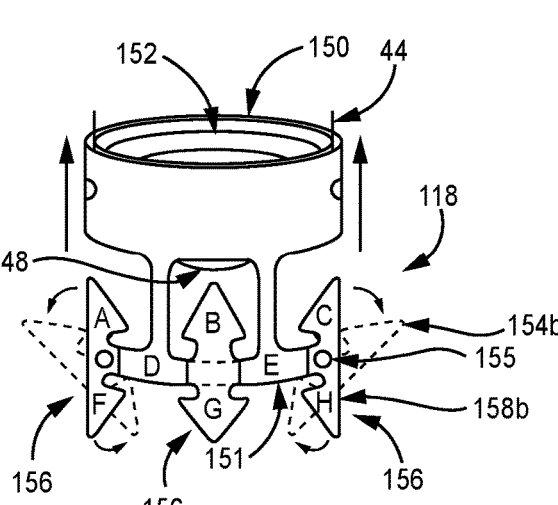
FIG. 11B is a schematic illustration of the anchor of FIG. 11A transitioning from the delivery arrangement to a deployed arrangement.
Figure 11C:
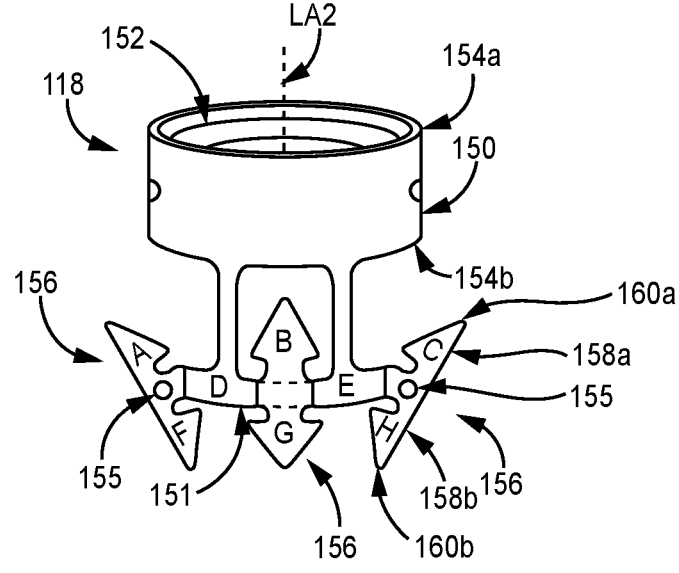
FIG. 11C is partial, enlarged side view of the anchor of FIG. 11A in the deployed arrangement.

Many anchor configurations of the disclosure can be utilized with the device and methods of FIGS. 10A-10E. In the example of FIGS. 10A-11C, each anchor 118 includes a body 150 having a proximal end 152*a* and a distal end 152*b* and an opening 152 extending from the proximal end 152*a* to the distal end 152*b*. The opening 152 is configured to receive a rod, such as any disclosed variation of rod 44. The opening 152 can optionally be threaded and configured to receive a threaded rod. In this example, the body 150 includes a plurality of slits or cuts to form a plurality of flanges 156 (e.g., four flanges), each having one proximal barb 158a having a pointed tip 160a and one distal barb 158ba each having a pointed tip 160b. In one example, the flanges 156 are made of a shape memory material and are configured to be biased such that the distal barbs 158b collectively form a pointed tip of the anchor 118 and the proximal flanges flare outwardly away from the longitudinal axis LA2 of the opening 152 as is shown in FIG. 11C. In one optional example, each flange 156 can be secured to or extend from a support ring 151 of the body 150 with a biased hinge 155. When the rod 44 is inserted within the opening 152 as is shown in FIG. 11A, the rod 44 pushes the distal barbs 158b outwardly and the proximal barbs 158a inwardly so that the anchor 118 can be delivered into tissue T. Once the rod 44 is removed, the anchor 118 transitions to its natural arrangement (FIG. 11C) having the proximal barbs 158a flared outwardly away from the longitudinal axis LA2. Should retrieval of the anchor 118 be desired, the rod 44 can be reinserted into the opening 152 to push the distal barbs 158b outwardly away from their biased orientation to correspondingly pull the proximal barbs 158a inwardly and disengage the proximal barbs 158a and anchor 118 from tissue T. In yet another example, it is envisioned that micro-machining can be used to create anchors with integrated small-scale hinges at the flange pivot points or to form hinges in the flanges.

Figure 12:
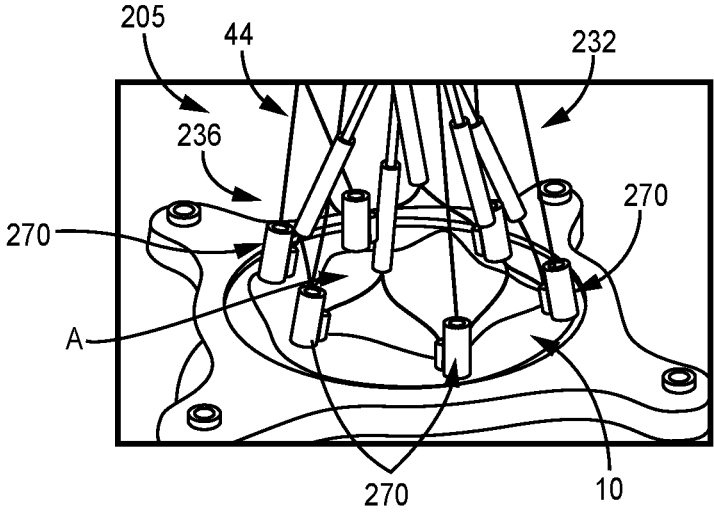
FIG. 12 is a partial, side view of an alternate system of the disclosure having a delivery device including a plurality of anchor housings for securing an implant of the system to tissue, such as a mitral valve annulus.

Referring now in addition to FIG. 12, which illustrate yet another system 205 of the disclosure including a delivery device 232 and the implant 10 of FIGS. 1-2 positioned around annulus A. In this example, the delivery device 232 includes a plurality of interconnected anchor housings 270, each anchor housing 270 configured to house one anchor, which are not visible in FIG. 12 (e.g., anchor 118 of FIGS. 11A-11C). Only a select few of the anchor housings 270 are referenced for ease of illustration. The present disclosure is not intended to be limited to any specific number of anchor housings 270. Additional details of the delivery device 232 can be found in U.S. Provisional Application Ser. No. 63/192,917, the disclosure of which is hereby incorporated by reference in its entirety. As with previous embodiments, the delivery device 232 can include one or more anchor delivery apparatuses 236 (only one of which is referenced for ease of illustration) including the rod 44, which can be of any of the variations disclosed herein. Each rod 44 can optionally include the depressible tab 60 or the like to maintain the position of the anchor 118 during delivery and/or to assist in proximally pulling the anchor 118 from tissue during retrieval. In this embodiment, one rod 44 can be used to deploy each anchor 118 from each anchor housing 270, one at a time. Alternatively, a plurality of rods 44 can be provided to deploy numerous anchors from their respective anchor housings 270 simultaneously, if desired. Other anchor configurations can be similarly used with this delivery device 232 and the present techniques.

The implant 10 and anchor housings 270 of FIG. 12, can alternatively be configured as shown in FIGS. 13 and 14, respectively. In this example, implant 310 includes a plurality of anchors 318 (only one is shown) of any of the types disclosed herein interconnected by a cinching member 316 such as a cord, wire, filament or the like. To accommodate the cinching member 316, each anchor housing 370 can include a body 372 defining a main opening 374 and defining two slots 376 approximately 180 degrees from each other to receive the cinching member 316. FIG. 15 is also referenced, which illustrates one anchor 318 of the implant 310 positioned within one anchor housing 370. In this example, the cinching member 316 interconnects the plurality of anchors 318 so that after each of the anchors have been deployed into tissue, such as the annulus A of FIGS. 1-2, the cinching member 316 can be proximally tensioned and locked in position to correspondingly resize the annulus or tissue in which the anchors are deployed. In such an example, one or more anchors 318 of the implant 310 can be configured as shown in FIG. 13. In this example, each anchor 318 includes a body 350 defining an opening 352 spanning between a proximal end 354a and a distal end 345b of the body 350. The body 350 further includes a plurality of slits that collectively form flanges 356, each having a proximal barb 358a opposing a distal barb 358b. Each barb 358a, 358b can terminate at a pointed tip 360a, 360b. Each flange 356 can be biased to a natural, deployed arrangement in which the distal barbs 358b converge toward a longitudinal axis LA3 of the opening 352. Generally, the flanges 356 can be configured similarly and function similarly as compared to flanges 56 or 156 disclosed herein. When in the anchor housing 370, the proximal barbs 358a are forced inwardly toward the longitudinal axis LA3, which correspondingly pushes the distal barbs 358b outwardly to the orientation shown in FIG. 15. In this way, the body 350 takes a generally cylindrical configuration. The cinching member 316 is configured to be aligned in the slots 376 in the anchor housing body 372 so that the cinching member 316 can interconnect the anchors 318 while the anchors 318 are positioned within their respective anchor housings 370 prior to deployment.

It is envisioned that the rods and/or anchors of the disclosure can be configured for recapture of the anchor in many ways. For example, an alternate rod and body of an anchor can include corresponding threads that allow for engagement of anchor via rotation of the rod and removal of the anchor via proximally withdrawing the rod. In such an example, the threaded portion of the anchor body would be deployed so that the treaded portion sits above the tissue for later engagement by the rod. Similar to prior disclosed embodiments, insertion of the rod into the main opening of the anchor proximate the distal end would force the proximal barbs inwardly, disengaging the proximal barbs from the tissue.

Figure 16:
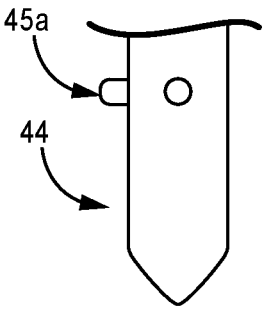
FIG. 16 is a partial, schematic view of the rod of the disclosure having an optional protrusion.
Figure 17:
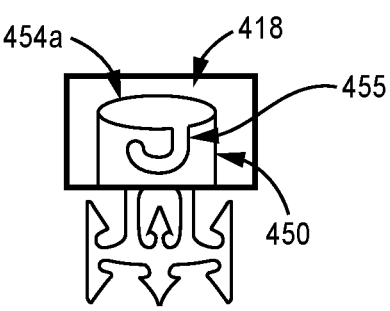
FIG. 17 is a schematic illustration of an alternate anchor having a body that can be engaged with the rod of FIG. 16.
Figure 18:
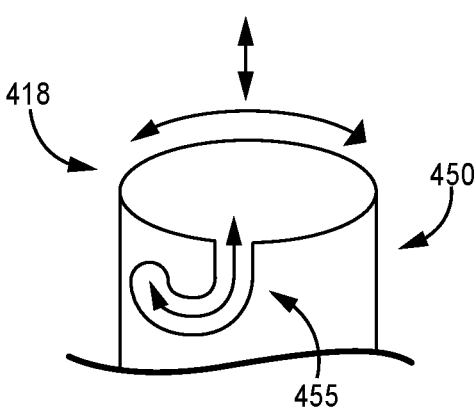
FIG. 18 is a schematic illustration showing a path of the protrusion of FIG. 16 to engage the rod with the anchor body of FIG. 17.

Referring now in addition to FIGS. 16-18, in this example, a proximal end 454a of a body 450 of an anchor 418 may include a slot 455. Any variation of the rod 44 of the disclosure can include a complimentary feature 45a, such as a protrusion, that is able to move through the slot 455. In this way, the rod 44 could be reinserted into the anchor 418, pushing distal barbs 458b outwardly to correspondingly push the proximal barbs 258a inwardly to disengage from tissue. At the same time, the rod 44 could be advanced and rotated within the slot 455 of the anchor 418, allowing the anchor to then be pulled proximally and removed from the tissue. The rod 44 and anchor 418 can otherwise be identically configured as compared with any other rod or anchor disclosed.

Referring now in addition to the concepts of FIGS. 19-22, which illustrate that a proximal end of any of the anchors (e.g., anchor 18) of the disclosure can include a retention feature on an interior surface of the body 50, such as a deformable ridge 51. A rod, such as rod 44, can include a corresponding feature, such as an indention 45b (FIG. 20), annular step 45c (FIG. 21) or annular protrusion 45d (FIG. 22). In this way, as the rod 44 is reinserted into the body opening 52 for retrieval of the anchor 18 and the distal barbs 58b are pushed outwardly, correspondingly pushing the proximal barbs 58*a* inwardly, the feature 45*b*, 45*c*, 45*d* can move past and catch on the ridge 51. Then, when the rod 44 is pulled proximally, the anchor 18 will correspondingly move proximally to pull the anchor 18 from the tissue. In some examples, the anchor retention feature 51 and rod feature 45*b*, 45*c* or 45*d* can be configured to only engage in a particular direction or orientation. It is to be understood that such principles can be applied to any embodiments of the disclosure, as desired.

Although anchors of the disclosure are largely disclosed as being made of an elastic or shape memory material such as nitinol, it is also envisioned that the anchors of the disclosure can be made of any biocompatible super-elastic material/alloy that would allow the barbs to be temporary held in a coplanar state with an axis of the anchor for delivery and then freed to assume an angled stated with the central axis of the anchor to engage tissue when deployed. In various embodiments, the barbs are not deformed when they are in the delivery arrangement, coplanar to the central, longitudinal axis of the anchor body. It is further envisioned that the anchors can be made of any material that is used in the manufacture of making springs, provided that the material is biocompatible. This can include spring steel or stainless steel. As with springs for other applications, this material could be heat-treated or otherwise treated to provide the anchor a natural configuration (i.e. a configuration that the anchor assumes when freed from external forces). The anchor can also include a combination of materials referenced herein. One non-limiting example includes NiTi body having hinges interconnecting the barbs to the body, the hinges made of spring steel. In some embodiments, the hinge could include a coiled spring hinge.

In the alternate anchor 518 of FIG. 23, the anchor 518 can be of any of the type disclosed herein except as explicitly stated. In this example, the anchor 518 can achieve biased flanges 556 with springs 555 secured to each flange. Similar to previously disclosed embodiments, the anchor 518 includes a plurality of flanges 556 that are biased such that distal barbs 558*b* of each flange are biased toward a longitudinal axis LA4 of the anchor 518. Only one distal barb 558*b* is referenced for ease of illustration, however, each flange 556 can be similarly configured as compared to any of those disclosed herein. In this example, however, each flange 556 is biased with one respective coiled spring 555 having a first end 580*a* and a second end 580*b* and a lumen 582 formed by coils of the spring 555 (see also, FIG. 24). One end 580*b* can be secured to support ring 551 (or the portion of the anchor body that surrounds the support ring, noted as D and E in FIG. 23) and the other end 580*a* can be secured to the distal barb 558*b*. The coil lumen 582 can be routed around a support ring 551 of the anchor. In a natural, deployed arrangement, the distal barbs 558*b* converge toward the longitudinal axis LA4 while proximal barbs 558*a* flare outwardly with respect to the longitudinal axis LA4 (see also, FIGS. 7B and 11C, for example). Alternatively, the spring 555 could also be secured to the proximal barb 558*a*, wherein the spring 555 is orientated such that the spring 555 biases the proximal barb 558*a* outwardly. The anchor 518 can be used in any systems of the disclosure in a manner similar to other anchors disclosed herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A system comprising:
an anchor including a body having a distal end, a proximal end and an opening extending from the proximal end to the distal end; wherein the distal end includes a plurality of flanges, each flange including a proximal barb and a distal barb; the anchor having a natural arrangement in which the distal barbs of the plurality of flanges converge to form a pointed tip; and
a rod; wherein the rod can be inserted in the opening to force the distal barbs away from a longitudinal axis of the opening into a delivery arrangement.

2. The system of claim 1, wherein the rod has a tapered tip.

3. The system of claim 1, wherein, in the natural arrangement, the proximal barbs are flared outwardly with respect to the longitudinal axis as compared to the delivery arrangement.

4. The system of claim 1, wherein the proximal and distal flanges are parallel to the longitudinal axis in the delivery arrangement.

5. The system of claim 1, wherein at least one flange includes a hinge.

6. The system of claim 1, wherein the rod includes a lip that is positioned proximal to the anchor.

7. The system of claim 1, wherein the rod includes a depressible tab.

8. The system of claim 1, wherein the anchor is one of a plurality of anchors stacked onto the rod.

9. The system of claim 1, wherein the anchor is one of a plurality of anchors, the plurality of anchors interconnected by a cinching member.

10. A method comprising:
providing a delivery device including an anchor and an anchor delivery apparatus including a rod having a distal tip: the anchor including a body having a distal end, a proximal end and an opening extending from the proximal end to the distal end: wherein the distal end includes a plurality of flanges, each flange including a proximal barb and a distal barb; wherein the rod is inserted through the opening such that the distal barbs and proximal barbs are positioned along an outer surface of the rod in a delivery arrangement;
positioning the distal tip of the rod at a first location at tissue within a human body;
distally advancing the anchor off of the rod and at least partially into the tissue such that the anchor transitions to a natural arrangement in which the proximal barbs engage the tissue and the distal barbs converge toward a longitudinal axis of the opening;
distally advancing the rod into the opening to force the distal barbs away from the longitudinal axis of the opening and the proximal barbs toward the longitudinal axis of the opening; and
repositioning the anchor.

11. The method of claim 10, wherein the anchor is distally advanced off of the rod and through an annuloplasty implant and into the tissue, the tissue being a valve annulus.

12. The method of claim 10, wherein the rod includes a lip that engages the anchor as the anchor is distally advanced.

13. The method of claim 10, wherein the anchor is one of a plurality of anchors that are stacked on the rod.

14. The method of claim 10, wherein the rod includes a depressible tab engaging the anchor and positioned distal to the anchor as the distal tip of the rod is positioned at the tissue.

15. The method of claim 14, wherein the step of positioning the distal tip of the rod at the first location includes inserting the distal tip into the tissue to depress the tab.

16. The method of claim 14, wherein the tab engages the anchor during the step of repositioning the anchor.

17. The method of claim 10, wherein at least one flange includes a hinge.

18. The method of claim 10, wherein the delivery device includes a plurality of anchor housings and the anchor is one of a plurality of anchors; wherein each anchor is positioned in one anchor housing.

19. The method of claim 18, wherein each anchor is interconnected by a cinching member.

20. The method of claim 10, wherein the distal barbs converge to form a pointed tip in the natural arrangement.

\*    \*    \*    \*    \*